(12) United States Patent
Shiran et al.

(10) Patent No.: US 11,478,222 B2
(45) Date of Patent: Oct. 25, 2022

(54) METHOD AND SYSTEM FOR ULTRASOUND IMAGING MULTIPLE ANATOMICAL ZONES

(71) Applicant: GE Precision Healthcare LLC, Wauwatosa, WI (US)

(72) Inventors: Carmit Shiran, Haifa (IL); Cynthia A Owen, Powhatan, AR (US); Mor Vardi, Haifa (IL)

(73) Assignee: GE Precision Healthcare LLC, Wauwatosa, WI (US)

( * ) Notice: Subject to any disclaimer, the term of this patent is extended or adjusted under 35 U.S.C. 154(b) by 275 days.

(21) Appl. No.: 16/419,419

(22) Filed: May 22, 2019

(65) Prior Publication Data

US 2020/0367859 A1 Nov. 26, 2020

(51) Int. Cl.
*A61B 8/00* (2006.01)
*A61B 8/08* (2006.01)
*A61B 8/14* (2006.01)

(52) U.S. Cl.
CPC .............. *A61B 8/46* (2013.01); *A61B 8/0841* (2013.01); *A61B 8/483* (2013.01); *A61B 8/488* (2013.01); *A61B 8/14* (2013.01); *A61B 8/4263* (2013.01); *A61B 8/481* (2013.01); *A61B 8/5207* (2013.01); *A61B 8/565* (2013.01)

(58) Field of Classification Search
None
See application file for complete search history.

(56) References Cited

U.S. PATENT DOCUMENTS

| 10,610,310 | B2 * | 4/2020 | Todd | H04N 5/44504 |
| 2010/0123831 | A1 * | 5/2010 | Crucs | A61C 9/004 |
| | | | | 348/715 |
| 2010/0179428 | A1 * | 7/2010 | Pedersen | G09B 23/286 |
| | | | | 600/443 |
| 2018/0000453 | A1 * | 1/2018 | Hunter | A61B 8/5207 |
| 2019/0142388 | A1 * | 5/2019 | Gonyeau | A61B 8/5215 |
| | | | | 600/407 |

* cited by examiner

*Primary Examiner* — Amanda Lauritzen Moher
*Assistant Examiner* — Delia M. Appiah Mensah (57) ABSTRACT

A method and ultrasound imaging system for performing an ultrasound examination. The method and system includes entering a workflow and displaying a plurality of graphical icons positioned on a graphical model. The method and system includes selecting a first anatomical zone, acquiring a first image, and saving and associating the first image with the first anatomical zone. The method and system includes saving and associating a first clinical finding with the first anatomical zone. The method and system includes selecting a second anatomical zone, acquiring a second image, and saving and associating the second image with the second anatomical zone. The method and system includes saving and associating a second clinical finding with the second anatomical zone. The method and system include displaying an examination overview including the first image, the first clinical finding, the second image, and the second clinical finding.

20 Claims, 4 Drawing Sheets

METHOD AND SYSTEM FOR ULTRASOUND IMAGING MULTIPLE ANATOMICAL ZONES

FIELD OF THE INVENTION

This disclosure relates generally to a method and system for performing an ultrasound workflow that requires imaging a plurality of anatomical zones.

BACKGROUND OF THE INVENTION

Many ultrasound workflows require storing both one or more images and a clinical finding for each of a plurality of different anatomical zones. Workflows on conventional ultrasound imaging systems require the user to navigate through a variety of different menus in order to select and associate the appropriate images and clinical findings with each of the different anatomical areas. For instance, many conventional ultrasound imaging systems display all of the saved images on a single clipboard or within a common library. The user must then navigate within the clipboard or library in order to locate and select the images for each of the different anatomical zones. It is oftentimes difficult for the user to quickly and accurately identify the specific images on the clipboard or in the library that were acquired from the desired anatomical zone. In additional to the laborious and error-prone task of identifying the images for each of the anatomical zones, the user must navigate through multiple menus in order to associate the correct clinical finding for each of the desired anatomical zones. The user may associate the clinical findings with the anatomical zones after the ultrasound acquisition has been completed. This additionally raises the risk of accidentally omitting either an image or a clinical finding for one or more of the anatomical zones in the workflow. For at least these reasons, there is a need for an improved method and ultrasound imaging system for performing an ultrasound examination.

BRIEF DESCRIPTION OF THE INVENTION

The above-mentioned shortcomings, disadvantages and problems are addressed herein which will be understood by reading and understanding the following specification.

In an embodiment, a method for performing an ultrasound examination includes entering a workflow that requires imaging a plurality of anatomical zones and displaying a graphical user interface on a display device. The graphical user interface includes a graphical model representing at least a portion of a patient and a plurality of graphical icons positioned on the graphical model, wherein each of the graphical icons represents a unique one of the plurality of anatomical zones. The plurality of graphical icons includes a first graphical icon and a second graphical icon. The method includes selecting a first anatomical zone, acquiring a first image with the ultrasound probe, saving and associating a first image with the first anatomical zone while the first anatomical zone is selected. The method includes saving and associating a first clinical finding with the first anatomical zone while the first anatomical zone is selected. The method includes selecting a second anatomical zone, acquiring a second image with the ultrasound probe, saving and associating a second image with the second anatomical zone while the second anatomical zone is selected, and saving and associating a second clinical finding with the second anatomical zone while the second anatomical zone is selected. The method includes displaying an examination overview including at least the first image, the first clinical finding, the second image, and the second clinical finding.

In an embodiment, an ultrasound imaging system includes an ultrasound probe, a display device, and a processor in electronic communication with the ultrasound probe and the display device. The processor is configured to receive instructions to enter a workflow that requires imaging a plurality of anatomical zones, and display a graphical user interface on the display device. The graphical user interface includes a graphical model representing at least a portion of a patient, a plurality of graphical icons positioned on the graphical model, wherein the plurality of graphical icons includes a first graphical icon and a second graphical icon, and wherein each of the plurality of graphical icons represents a unique one of the plurality of anatomical zones. The processor is configured to receive a selection of the first anatomical zone, control the ultrasound probe to acquire a first image, and save and associate the first image with the first anatomical zone while the first anatomical zone is selected. The processor is configured to save and associate a first clinical finding with the first anatomical zone. The processor is configured to receive a selection of the second anatomical zone, control the ultrasound probe to acquire a second image, and save and associate the second image with the second anatomical zone while the second anatomical zone is selected. The processor is configured to save and associate a second clinical finding with the second anatomical zone while the second anatomical zone is selected. The processor is configured to display an examination overview on the display device, wherein the examination overview comprises at least the first image, the first clinical finding, the second image, and the second clinical finding.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
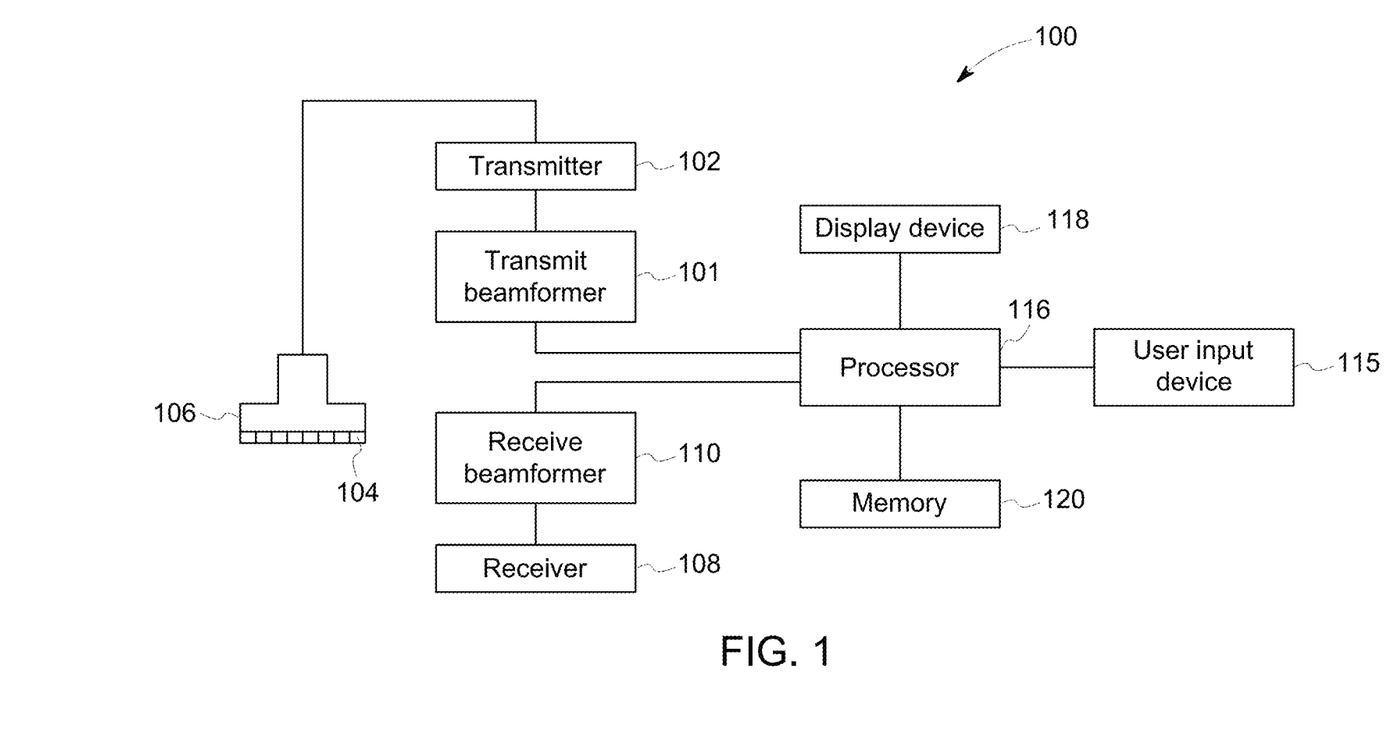
FIG. 1 is a schematic diagram of an ultrasound imaging system in accordance with an embodiment.

FIG. 1 is a schematic diagram of an ultrasound imaging system 100 in accordance with an embodiment. The ultrasound imaging system 100 includes a transmit beamformer 101 and a transmitter 102 that drive elements 104 within an ultrasound probe 106 to emit pulsed ultrasonic signals into a body (not shown). The ultrasound probe 106 may be a linear probe, a curved linear probe, a 2D array, a mechanical 3D/4D probe, or any other type of ultrasound probe capable of acquiring ultrasound data. Still referring to FIG. 1, the pulsed ultrasonic signals are back-scattered from structures in the body, like blood cells or muscular tissue, to produce echoes that return to the elements 104. The echoes are converted into electrical signals by the elements 104 and the electrical signals are received by a receiver 108. The electrical signals representing the received echoes are passed through a receive beamformer 110 that outputs ultrasound data. According to some embodiments, the ultrasound probe 106 may contain electronic circuitry to do all or part of the transmit and/or the receive beamforming. For example, all or part of the transmit beamformer 101, the transmitter 102, the receiver 108 and the receive beamformer 110 may be situated within the ultrasound probe 106. The terms "scan" or "scanning" may also be used in this disclosure to refer to acquiring data through the process of transmitting and receiving ultrasonic signals. The terms "data" or "ultrasound data" may be used in this disclosure to refer to either one or more datasets acquired with an ultrasound imaging system. A user input device 115 may be used to control operation of the ultrasound imaging system 100, including, to control the input of patient data, to set an acquisition preset, or to change a display parameter, and the like. The user input device 115 may include components such as a keyboard, a mouse, a track ball, a track pad, a touch screen, a multi-touch screen, and the like.

The ultrasound imaging system 100 also includes a processor 116 to control the transmit beamformer 101, the transmitter 102, the receiver 108 and the receive beamformer 110. The processor 116 is in electronic communication with the ultrasound probe 106. The processor 116 may control the ultrasound probe 106 to acquire data. The processor 116 controls which of the elements 104 are active and the shape of a beam emitted from the ultrasound probe 106. The processor 116 is also in electronic communication with a display device 118, and the processor 116 may process the data into images or values for display on the display device 118. The display device 118 may comprise a monitor, an LED display, a cathode ray tube, a projector display, or any other type of apparatus configured for displaying an image. Additionally, the display device 118 may include one or more separate devices. For example, the display device 118 may include two or more monitors, LED displays, cathode ray tubes, projector displays, etc. The display device 118 may also be a touchscreen. For embodiments where the display device 118 is a touchscreen, the touchscreen may function as an input device and it may be configured to receive touch or touch gesture inputs from a user. For purposes of this disclosure, the term "electronic communication" may be defined to include both wired and wireless connections. The processor 116 may include a central processor (CPU) according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, an FPGA, and a graphic board. According to another embodiment, the processor 116 may also include a complex demodulator (not shown) that demodulates the RF data and generates raw data. In another embodiment the demodulation can be carried out earlier in the processing chain. The processor 116 may be adapted to perform one or more processing operations according to a plurality of selectable ultrasound modalities on the data. The data may be processed in real-time during a scanning session as the echo signals are received. For the purposes of this disclosure, the term "real-time" is defined to include a procedure that is performed without any intentional delay. For purposes of this disclosure, the term "real-time" will additionally be defined to include an action occurring within 2 seconds. For example, if data is acquired, a real-time display of that data would occur within 2 seconds of the acquisition. Those skilled in the art will appreciate that most real-time procedures/processes will be performed in substantially less time than 2 seconds. The data may be stored temporarily in a buffer (not shown) during a scanning session and processed in less than real-time in a live or off-line operation.

Some embodiments of the invention may include multiple processors (not shown) to handle the processing tasks. For example, a first processor may be utilized to demodulate and decimate the RF signal while a second processor may be used to further process the data prior to displaying an image. It should be appreciated that other embodiments may use a different arrangement of processors.

The ultrasound imaging system 100 may continuously acquire data at a given frame-rate or volume-rate. Images generated from the data may be refreshed at a similar frame-rate or volume-rate. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

Optionally, embodiments of the present invention may be implemented utilizing contrast agents. Contrast imaging generates enhanced images of anatomical structures and blood flow in a body when using ultrasound contrast agents including microbubbles. After acquiring data while using a contrast agent, the image analysis includes separating harmonic and linear components, enhancing the harmonic component and generating an ultrasound image by utilizing the enhanced harmonic component. Separation of harmonic components from the received signals is performed using suitable filters. The use of contrast agents for ultrasound imaging is well-known by those skilled in the art and will therefore not be described in further detail.

In various embodiments of the present invention, data may be processed by other or different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate and combinations thereof, and the like. The image beams and/or frames are stored and timing information indicating a time at which the data was acquired in memory may be recorded. The modules may include, for example, a scan conversion module to perform scan conversion operations to convert the image frames from coordinates beam space to display space coordinates. A video processor module may be provided that reads the image frames from a memory and displays the image frames in real time while a procedure is being carried out on a patient. A video processor module may store the image frames in an image memory, from which the images are read and displayed.

Figure 2:
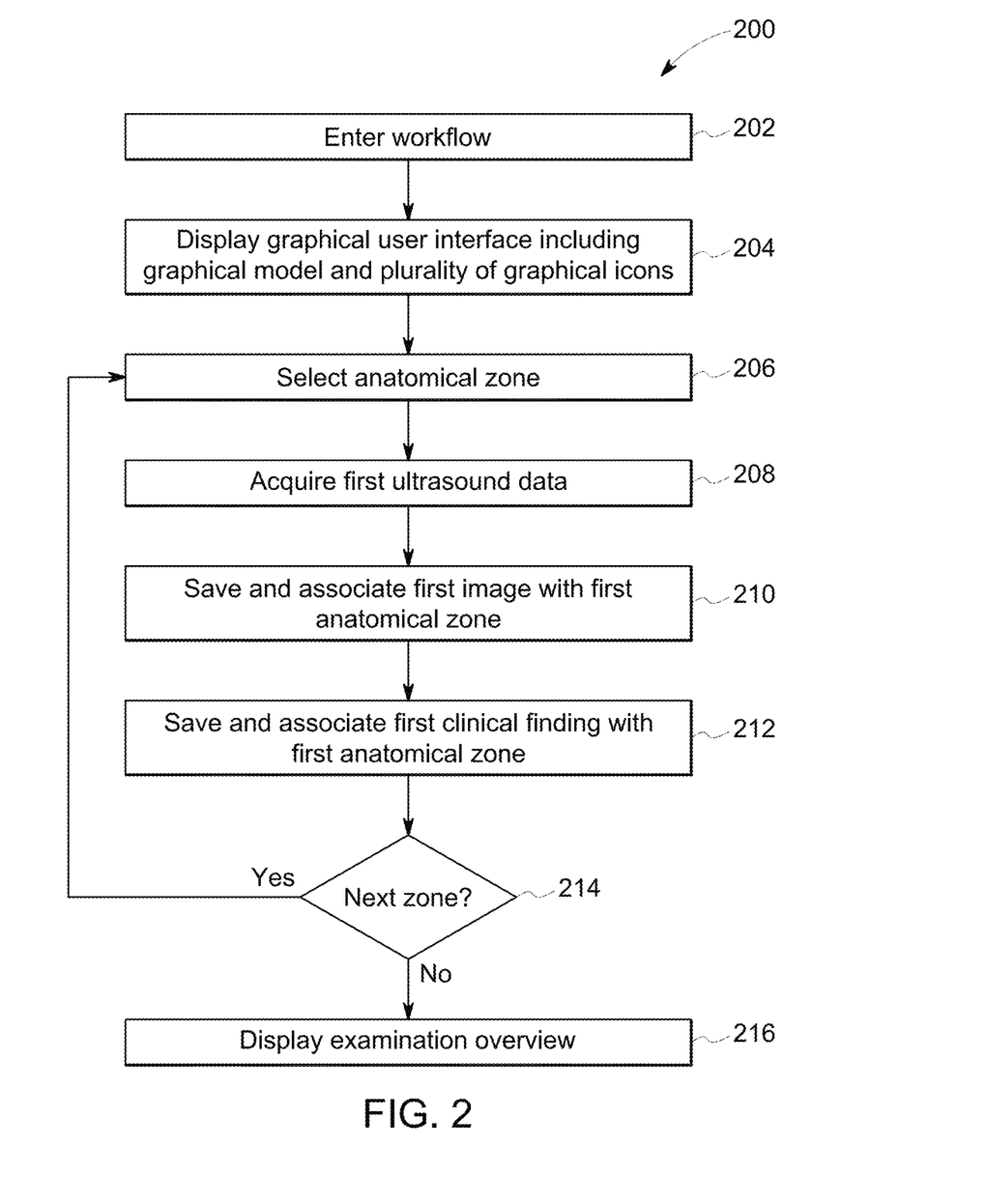
FIG. 2 is a flow chart of a method in accordance with an embodiment.

FIG. 2 is a flow chart of a method 200 in accordance with an exemplary embodiment. The individual blocks of the flow chart represent steps that may be performed in accordance with the method 200. Additional embodiments may perform the steps shown in a different sequence and/or additional embodiments may include additional steps not shown in FIG. 2. The technical effect of the method 200 is the display of an examination overview comprising at least a first image, a first clinical finding, a second image, and a second clinical finding. The method 200 may be performed with the ultrasound imaging system 100 shown in FIG. 1. The method 200 will be described in detail hereinafter.

At step 202, a user enters a workflow. The user may, for instance, interact with a graphical user interface displayed on the display device 118 in order to select the workflow. The method 200 will be described according to an exemplary embodiment where the workflow is an extended focused assessment with sonography in trauma (eFAST) workflow which is commonly used to identify the presence of free fluid in each of a plurality of different anatomical zones. The user may, for instance, select the eFAST workflow from a plurality of workflow options displayed in a drop-down menu. It should be appreciated that the selection of the workflow may be accomplished by selecting a soft button or interacting with the graphical user interface in a different manner in other embodiments.

Figure 3:
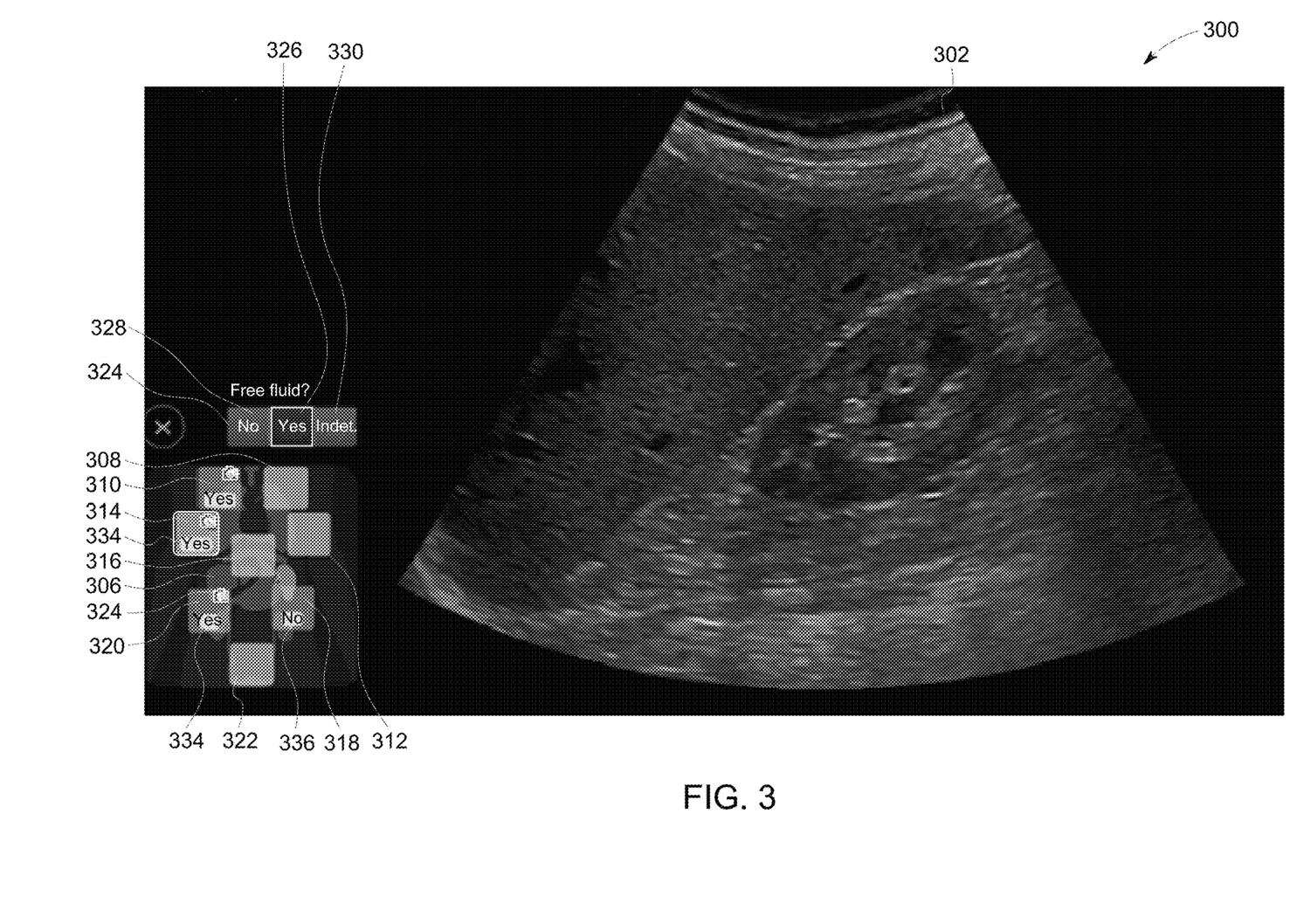
FIG. 3 is a screenshot in accordance with an embodiment.

At step 204, the processor 116 causes a graphical user interface to be displayed on the display device 118 that is specific to the selected workflow, which may be the eFAST workflow according to an exemplary embodiment. FIG. 3 is a screenshot 300 according to an exemplary embodiment. FIG. 3 includes an image 302 and a graphical user interface. The graphical user interface includes a graphical model 306 representing at least a portion of a patient. The graphical user interface includes a plurality of graphical icons positioned on the graphical model 306. The graphical user interface may include other elements according to various embodiments. For example, the graphical user interface may include drop-down menus, additional buttons or other graphical user interface icons with which a user may interact. According to the exemplary embodiment shown in FIG. 3 the graphical user interface may include a first graphical icon 308, a second graphical icon 310, a third graphical icon 312, a fourth graphical icon 314, a fifth graphical icon 316, a sixth graphical icon 318, a seventh graphical icon 320, and an eighth graphical icon 322 are shown positioned on the graphical model 306. Each of the graphical icons represents a different anatomical zone, and the position of each graphical icon with respect to the graphical model 306 indicates a corresponding anatomical zone. According to an embodiment, the first graphical icon 308 may correspond to an anterior left thorax zone, a second graphical icon 310 may correspond to an anterior right thorax zone, the third graphical icon 312 may correspond to a lateral left thorax zone, the fourth graphical icon 314 may correspond to a lateral right thorax zone, the fifth graphical icon 316 may correspond to a cardiac zone, the sixth graphical icon 318 may correspond to an left upper quadrant zone, the seventh graphical icon 320 may correspond to a right upper quadrant zone, and the eighth graphical icon 322 may correspond to a pelvis zone.

At step 206, a first one of the plurality of anatomical zones is selected. According to an embodiment, the first one of the plurality of anatomical zones may be the anterior left thorax zone. The user may select the first one of the plurality of anatomical zones by selecting the corresponding graphical icon. For instance, the user may select the anterior left thorax zone by selecting the first graphical icon 308. As discussed previously, the user may select the first graphical icon 308 by using a mouse, a trackball, a touchpad, a touchscreen, or any other method of selecting a graphical icon that is part of the graphical user interface displayed on the display device 118. According to an exemplary embodiment where the display device 118 is a touchscreen, the user may select the first graphical icon 308 by touching the first graphical icon 308 displayed on the touchscreen. According to another embodiment, the processor 116 may automatically select a first one of the plurality of anatomical zones in response to entering the workflow during step 202.

According to an embodiment, the processor 116 may display a reference image showing an exemplary image of the selected anatomical zone in response to selecting the corresponding graphical icon. For example, the reference image may be of an exemplary ultrasound image of the anterior left thorax zone. Additionally, the processor 116 may display an image or a model demonstrating the placement of the ultrasound probe 106 needed to generate the desired image or images of the selected anatomical zone.

According to an embodiment, the processor 116 may automatically display a pop-up button 324 as part of the graphical user interface in response to selecting one of the anatomical zones at step 206. The pop-up button 324 is configured to allow the user to select multiple different clinical findings for the selected anatomical zone. The pop-up button 324 includes a first selectable portion 326 for indicating a positive clinical finding, a second selectable portion 328 for indicating a negative clinical finding, and a third selectable portion 330 for indicating an indeterminate clinical finding.

At step 208, the processor 116 controls the ultrasound probe 106 to acquire first ultrasound data. The user positions the ultrasound probe 106 to acquire the first ultrasound data corresponding to the anatomical zone selected during step 206. According to an exemplary embodiment, the user may position the ultrasound probe 106 to acquire the first ultrasound data from the left top lung zone.

According to the eFAST workflow, it is desired to determine if there is free fluid within each of the anatomical zones. The user may acquire ultrasound data within each of the anatomical zones until it is possible to make a determination about whether or not there is free fluid within a particular anatomical zone. According to some embodiments, the user may be able to make a determination regarding free fluid based on a single ultrasound image. However, according to other embodiments, multiple images may be required for the user to make an accurate determination for a particular anatomical zone.

At step 210, one or more images are saved for the selected anatomical zone. According to an embodiment, the user may interact with a command displayed on the graphical user interface to save and associate a first image or images with the selected anatomical zone. According to another embodiment, the first image or images may be automatically saved and associated with the first one of the plurality of anatomical zones in response to selecting a clinical finding for the selected anatomical zone as will be described in detail hereinafter.

At step 212, a clinical finding is saved and associated with the selected anatomical zone. When performing the eFAST workflow, the clinical finding is related to the presence of free fluid. According to an embodiment, the user may interact with the pop-up button 324 to select the clinical finding for the selected anatomical zone. For instance, the user may use one of a nonlimiting list including a mouse, a trackball, a touchpad, and a touchscreen to select one of the three selectable portions of the pop-up button 324 in order to save and associate a clinical finding with the selected anatomical zone. For instance, if there is evidence of free fluid within the ultrasound image or images acquired from the selected anatomical zone, the user may select the first selectable portion 326 of the pop-up button 324 to indicate a positive finding for free fluid. If there is not any evidence of free fluid within the ultrasound images acquired from the selected anatomical zone, the user may select the second selectable portion 328 of the pop-up button to indicate a negative finding for free fluid. If it is difficult or impossible for the user to determine if there is free fluid within the selected anatomical region, the user may select the third selectable portion 330 of the pop-up button to indicate an indeterminate finding for free fluid. As described hereinabove, according to an exemplary embodiment, the processor 116 may automatically store and associate both the clinical finding and the image currently being displayed with the selected anatomical zone in response to receiving a selection of clinical finding from the user. According to an embodiment where the anatomical zone selected at step 206 is the left top lung zone, the processor 116 would save and associate the image currently displayed and the clinical finding with the left top lung zone. This particular embodiment reduces the number of inputs required by the user to store and associate both the image and the clinical finding for a particular anatomical region in the 120.

Another embodiment may allow the user to save and associate multiple images with the selected anatomical zone. An embodiment may include a control in the user interface that allows the user to save more than one image with a particular anatomical zone. For instance, the user interface may include a control with "save" or a "store" command. And, once in the selected anatomical zone, the user may interact with the control to save multiple images with the selected anatomical zone. According to other embodiments, the user may save a cine clip of ultrasound images with the selected anatomical zone.

The processor 116 may display a first status indicator to indicate that an image has been saved and associated with the selected anatomical zone. The first status indicator may be an icon, a color or any other graphical technique used to indicate that an image has been saved and associated with the selected anatomical zone. According to the embodiment shown in FIG. 3, the first status indicator is a camera icon 329. The presence or absence of the first status indicator, such as the camera icon 329, in each of the graphical icons quickly conveys which anatomical zones have an associated image and the anatomical zones for which an image still needs to be acquired. The camera icon 329 is displayed with the second graphical icon 310, the fourth graphical icon 314 and the seventh graphical icon 320 in the embodiment displayed in FIG. 3. This conveys to the user that one or more images have been saved and associated with the anterior right thorax zone (corresponding to the second graphical icon 310); that one or more images have been saved and associated with the lateral right thorax zone (corresponding to the fourth graphical icon 314); and that one or more images have been saved and associated with the right upper quadrant (corresponding to the seventh graphical icon 320).

The processor 116 may also display additional status indicators in each of the graphical icons to indicate the clinical finding for the corresponding anatomical zone. According to an embodiment, the additional status indicators may be text strings. For instance, a first text string 334 may spell "yes" to indicate the presence of free fluid in the corresponding anatomical zone; a second text string 336 may spell "no" to indicate the absence of free fluid in the corresponding anatomical zone; and a third text string may spell "indeter." (not shown in FIG. 3) to indicate that the presence of free fluid in the corresponding anatomical zone is indeterminate.

According to the embodiment shown in FIG. 3, the first text string 334 is displayed with the second graphical icon 310, the fourth graphical icon 314, and the seventh graphical icon 320 to indicate the presence of free fluid in the anterior right thorax zone, the lateral right thorax zone, and the right upper quadrant zone. The second text string 336 is displayed with the sixth graphical icon 318 to indicate that no evidence of free fluid was found in the corresponding left upper quadrant zone. None of the graphical icons shown in FIG. 3 are labeled with the third text string in the embodiment shown in FIG. 3. It should be appreciated that other embodiments may use other ways to graphically indicate the clinical finding for anatomical zone corresponding to each of the graphical icons. For example, embodiments may use a second graphical icon to indicate a positive clinical finding. Embodiments may use text strings other than the text strings listed above. Embodiments may use a color or other graphical technique to graphically indicate which of the anatomical zones have a particular clinical finding. For example, the graphical icons corresponding to anatomical zones with a positive clinical finding may be presented in a first color while the graphical icons corresponding to anatomical zones with a negative clinical finding may be presented in a second color that is different from the first color.

Using additional status indicators to indicate the clinical finding of the anatomical zone associated with each of the graphical icons quickly conveys the clinical finding of each of the anatomical zones to the user. Additionally, the status indicators show which of the anatomical zones have been completed in the workflow.

If it is desired to acquire images and determine a clinical finding for another anatomical zone at step 214, then the method 200 returns to step 206. If it is not desired to acquire images and determine a clinical finding for another anatomical zone at step 214, then the method 200 advances to step 216, which will be described hereinafter.

According to an embodiment, the processor 116 may automatically or semi-automatically guide the user through the workflow in order to ensure that images have been acquired for each of the anatomical zones and that clinical findings have been determined for each of the anatomical zones. For instance, after the user has saved an image and a clinical finding for the first anatomical region, such as the top left lung region, the processor 116 may automatically advance to the next zone at step 206. For instance, according to an embodiment where the user is automatically guided through the workflow, the workflow may have a predetermined order through the plurality of anatomical zones and the processor 116 may automatically select the next anatomical zone in the predetermined order. For example, according to the embodiment shown in FIG. 3, the predetermined order for the anatomical zones may be the anterior left thorax zone, the anterior right thorax zone, the lateral left thorax zone, the lateral right thorax zone, the cardiac zone, the left upper quadrant zone, the right upper quadrant zone, and then the pelvis zone. It should be appreciated that workflow may include different anatomical zones, and/or the predetermined order may be different for other embodiments. According to an embodiment, the processor 116 may automatically select the anterior right thorax zone after the anterior left thorax zone has been completed.

According to an embodiment where the processor 116 semi-automatically guides the user through the workflow, the processor 116 may prompt the user to select the next anatomical zone. For example, the processor 116 may display a message instructing the user of the next anatomical zone to be selected. Or the processor 116 may provide another form of visual prompt. For example, the processor 116 my highlight the graphical icon corresponding to the next anatomical zone that should be selected. The processor 116 may use color or flashing to indicate the next graphical icon that should be selected at step 206.

According to an embodiment, another embodiment may use artificial intelligence, such as machine learning or a neural network, to identify the anatomical zone currently being scanned. For example, the user may initiate a scan and then the ultrasound imaging system 100 may use artificial intelligence to identify if the current ultrasound image is from one of the anatomical zones. If the current image is from one of the anatomical zones, the processor 116 may automatically select the corresponding anatomical zone, and then both the image and a clinical finding could be saved and associated with the anatomical zone that was identified through artificial intelligence. According to this embodiment, the user may acquire images from the various anatomical zones in any order and rely on artificial intelligence to recognize the anatomical zone currently being scanned. The artificial intelligence may be based on a plurality of curated training images representing the various anatomical zones in a specific workflow.

Referring back to the method 200 shown in FIG. 2, after selecting the anatomical zone at step 206, through one of a manual process, a semi-automated process, or a fully automated process, the method 200 continues. The method 200 may iteratively implement steps 206, 208, 210, 212 and 214 until the method has progressed through all of the anatomical zones in the workflow. According to some embodiments, the user may have the option of only saving and associating images for anatomical zones with a positive clinical finding. According to other embodiments, the user may only save and associate images for the anatomical zones with a positive or indeterminate clinical finding. According to an embodiment, the user may only save and associate images for the anatomical zones with a negative clinical finding. The processor 116 may graphically indicate the graphical icon of the current anatomical zone in the workflow. In the example shown in FIG. 3, the fourth graphical icon 314, indicating the lateral right lung zone, is graphically indicated by an outline 334. The outline 334 may be in a different color to make it easier for the user to identify the current anatomical zone. Other techniques may be used in other embodiments to graphically indicate the graphical icon of the current zone. A non-limiting list of techniques for graphically indicating one of the graphical icons includes highlighting, colorizing, increasing intensity, and increasing brightness.

Figure 4:
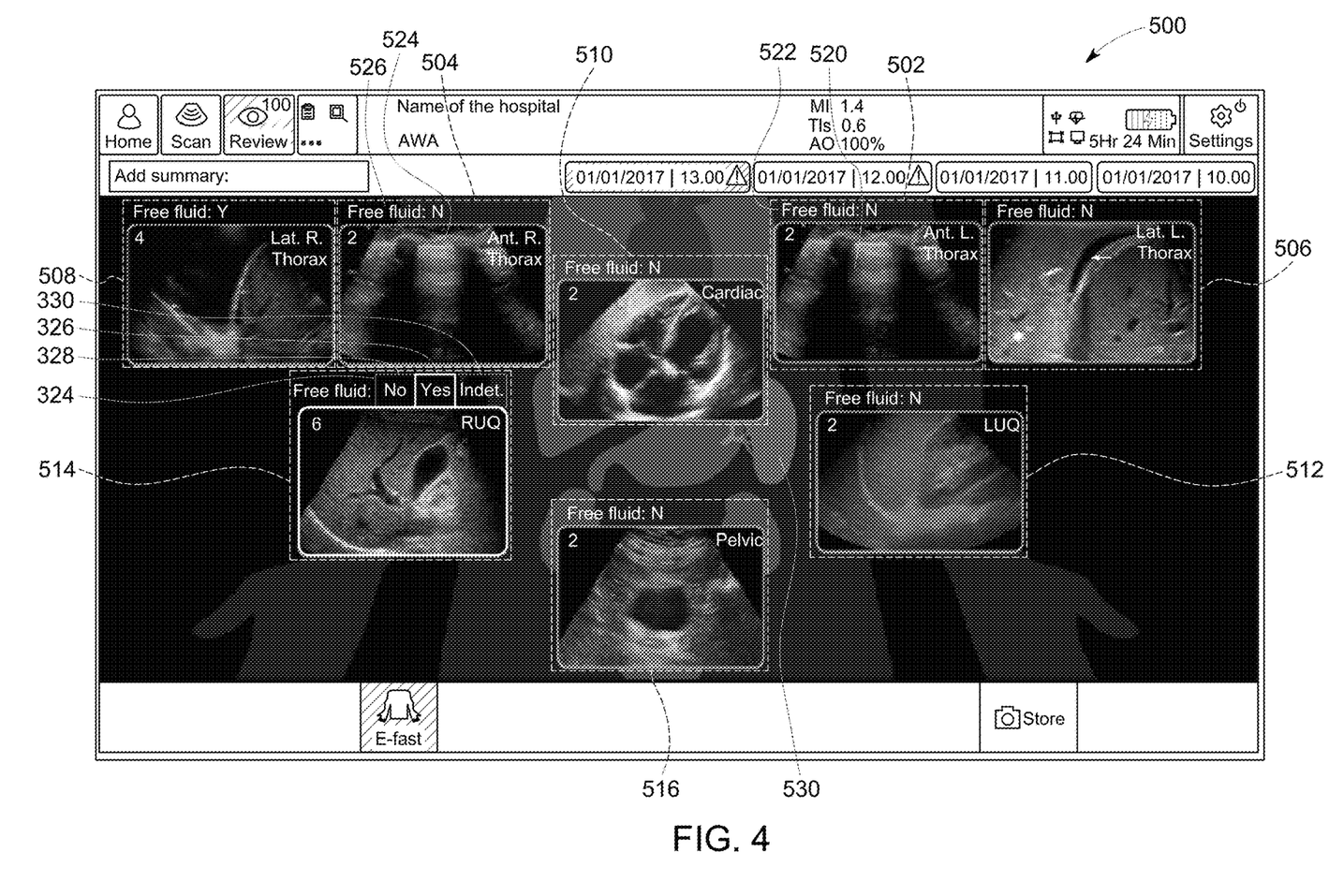
FIG. 4 is a screenshot in accordance with an embodiment.

After images and clinical findings have been associated with all of the steps in the workflow, at step 216, the processor 116 displays an examination overview including at least the first image and the first clinical finding and the second image and the second clinical finding at the same time. FIG. 4 is of an examination overview 500 according to an exemplary embodiment. The examination overview 500 includes a first tile 502, a second tile 504, a third tile 506, a fourth tile 508, a fifth tile 510, a sixth tile 512, a seventh tile 514, and an eighth tile 516. The first tile 502 corresponds to the first anatomical zone, the second tile 504 corresponds to the second anatomical zone, the third tile corresponds to the third anatomical zone, the fourth tile 508 corresponds to the fourth anatomical zone, the fifth tile 510 corresponds to the fifth anatomical zone, the sixth tile 512 corresponds to the sixth anatomical zone, the seventh tile 514 corresponds to the seventh anatomical zone, and the eighth tile corresponds to the eighth anatomical zone. Each of the tiles is configured to display at least one image associated with the corresponding anatomical zone and the associated clinical finding. For example, a first image 520 and the first clinical finding 522 are displayed in the first tile 502 and a second image 524 and the second clinical finding 526 are displayed in the second tile 504. The examination overview 500 includes a second graphical model 530 representing at least a portion of the patient. In the embodiment shown in FIG. 5, the second graphical model 530 is of at least a portion of the patient. The second graphical model 530 may be the same as the graphical model 306, or it may be different. The tiles are positioned with respect to the second graphical model 530 to help the user identify the corresponding anatomical zone. For example, the first tile 502 is positioned on the left side of the second graphical model 530 to indicate that it corresponds to the left top lung zone.

The examination overview 500 includes the text string "Free Fluid: Y" to indicate a positive clinical finding and the text string "Free Fluid: N" to indicate a negative clinical finding. For example, the first clinical finding 522 says "Free Fluid: Y" and the second clinical finding 526 says "Free Fluid: N". Other embodiments may use different techniques to present the clinical findings. For example, embodiments may use a first color to indicate a positive clinical finding and a second color to indicate a negative clinical finding. Embodiments may use one or more icons to denote the clinical finding and/or embodiments may display different text strings to identify the various clinical findings. By viewing the examination overview 500, the user can quickly and see the associated image and the associated clinical finding for each of the anatomical zones.

The examination overview 500 provides the user with concise summary of the workflow, which may be the eFAST workflow according to an embodiment. The examination overview 500 displays an image and a clinical finding for each of the anatomical zones. By displaying both an image and the clinical finding for each anatomical zone in the corresponding tile, the user can easily see the results of the workflow. For example, the user can see the associated image and clinical finding in a easy-to-interpret format.

According to an embodiment, the examination overview 500 may be used as an interface to make changes or adjustments to the image and/or the clinical finding associated with a specific anatomical zone. The user may change the clinical finding associated with one or more of the anatomical zones. The pop-up button 324, may, for instance, be used to change the clinical finding for the anatomical zone corresponding to the tile. The user may simply select a different clinical finding displayed in the pop-up button 324 using a user input device or through an interaction with a touchscreen.

If an image is incorrectly associated with the wrong anatomical zone, the user may also adjust change the association of the image. For example, the user may drag-and-drop the image from one tile to another. For example, an image displayed in the first tile 502 was incorrectly associated with the first anatomical zone, the user could drag that image from the first tile 502 to a different one of the plurality of tiles, such as the second tile 504. According to embodiments where the display device 118 is a touchscreen, the user may simply drag the image from one tile to another tile with a touch gesture through the touchscreen to change the anatomical zone to which the image is associated.

According to an embodiment with multiple images saved and associated with one or more of the anatomical zones, the user may view the various saved images from the examination overview. For instance, the user may swipe left or right on the tile to advance to the next image associated with the corresponding anatomical zone.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A method for performing an ultrasound examination, the method comprising:
    entering a workflow that requires imaging a plurality of anatomical zones;
    displaying a graphical user interface on a display device, wherein the graphical user interface comprises:
    a graphical model representing at least a portion of a patient;
    a plurality of graphical icons positioned on the graphical model, wherein the plurality of graphical icons includes a first graphical icon and a second graphical icon, and wherein each of the plurality of graphical icons represents a unique one of the plurality of anatomical zones;
    selecting a first anatomical zone;
    acquiring a first image with an ultrasound probe;
    saving and associating a first image with the first anatomical zone while said first anatomical zone is selected;
    saving and associating a first clinical finding with the first anatomical zone while said first anatomical zone is selected, wherein the first clinical finding is related to a presence of free fluid in the first anatomical zone;
    selecting a second anatomical zone;
    acquiring a second image with the ultrasound probe;
    saving and associating the second image with the second anatomical zone while said second anatomical zone is selected;
    saving and associating a second clinical finding with the second anatomical zone while said second anatomical zone is selected, wherein the second clinical finding is related to a presence of free fluid in the second anatomical zone;
    displaying an examination overview comprising a plurality of tiles and a second graphical model representing at least a portion of the patient on the display device, wherein each of the plurality of tiles corresponds to a different one of the plurality of anatomical zones and each of the plurality of tiles is displayed in a position with respect to the second graphical model to assist in the identification of a corresponding anatomical zone, wherein the first image and the first clinical finding are both displayed in a first tile of the plurality of tiles, and wherein the second image and the second clinical finding are both displayed in a second tile of the plurality of tiles.

2. The method of claim 1, wherein said selecting the second anatomical zone comprises selecting the second anatomical zone by interacting with the second graphical icon.

3. The method of claim 1, wherein said selecting the second anatomical zone is performed automatically after said saving and associating the first image and said saving and associating said first clinical finding with the first anatomical zone.

4. The method of claim 1, further comprising displaying a first status icon after said first image has been saved and associated with the first zone, wherein said first status icon indicates that the first image has been saved and associated with the first zone.

5. The method of claim 4, wherein the first status icon comprises a camera icon displayed in the first graphical icon.

6. The method of claim 1, further comprising displaying a pop-up button with a plurality of statuses for the first clinical finding in response to said selecting the first anatomical zone.

7. The method of claim 6, wherein the pop-up button includes a first status of a positive clinical finding and a second status of a negative clinical finding.

8. The method of claim 7, further comprising selecting one of the first status and the second status by manually interacting with the pop-up button, and wherein said saving and associating the first clinical finding with the first anatomical zone comprises saving and associating the one of the first status and the second status with the first anatomical zone.

9. The method of claim 1, wherein the workflow is an extended focused assessment with sonography in trauma workflow.

10. The method of claim 1, further comprising:
    acquiring additional images with the ultrasound probe while said first anatomical zone is selected;
    saving and associating the additional images with the first anatomical zone while said first anatomical zone is selected; and
    inputting one or more swipe gestures on the first tile to advance from the first image to one of the additional images associated with the first anatomical zone.

11. The method of claim 1, further comprising using a neural network to determine the first clinical finding for the first anatomical zone and using the neural network to determine the second clinical finding for the second anatomical zone.

12. An ultrasound imaging system comprising:
    an ultrasound probe;
    a display device; and
    a processor in electronic communication with the ultrasound probe and the display device, wherein the processor is configured to:
    receive instructions to enter a workflow that requires imaging a plurality of anatomical zones;
    display a graphical user interface on the display device, wherein the graphical user interface comprises:
    a graphical model representing at least a portion of a patient;
    a plurality of graphical icons positioned on the graphical model,
    wherein the plurality of graphical icons includes a first graphical icon and a second graphical icon, and wherein each of the plurality of graphical icons represents a unique one of the plurality of anatomical zones;
receive a selection of the first anatomical zone;
control the ultrasound probe to acquire a first image;
save and associate the first image with the first anatomical zone while the first anatomical zone is selected;
save and associate a first clinical finding with the first anatomical zone while the first anatomical zone is selected, wherein the first clinical finding is related to a presence of free fluid in the first anatomical zone;
receive a selection of the second anatomical zone;
control the ultrasound probe to acquire a second image;
save and associate the second image with the second anatomical zone while the second anatomical zone is selected;
save and associate a second clinical finding with the second anatomical zone while the second anatomical zone is selected, wherein the second clinical finding is related to a presence of free fluid in the second anatomical zone;
display an examination overview comprising a plurality of tiles and a second graphical model representing at least a portion of the patient on the display device, wherein each of the plurality of tiles corresponds to a different one of the plurality of anatomical zones and each of the plurality of tiles is displayed in a position with respect to the second graphical model to assist in the identification of a corresponding anatomical zone, wherein the first image and the first clinical finding are both displayed in a first tile of the plurality of tiles, and wherein the second image and the second clinical finding are both displayed in a second tile of the plurality of tiles.

13. The ultrasound imaging system of claim 12, wherein the processor is further configured to display a first status icon to indicate that the first image has been saved and associated with the first zone.

14. The ultrasound imaging system of claim 13, wherein the processor is configured to automatically select the second anatomical zone after the first image and the first clinical finding have been saved and associated with the first anatomical zone.

15. The ultrasound imaging system of claim 12, wherein the processor is configured to adjust the association of the first image to the first anatomical zone based on a command received while the examination overview is displayed.

16. The ultrasound imaging system of claim 15, wherein the command comprises dragging the first image to one of the plurality of tiles associated with a different one of the plurality of anatomical zones.

17. The ultrasound imaging system of claim 15, wherein the processor is configured to adjust the either the first clinical finding or the second clinical finding while the examination overview is displayed.

18. The ultrasound imaging system of claim 12, wherein the processor is configured to save and associate the first clinical finding with the first anatomical zone in response to an input received through a pop-up button displaying a plurality of statuses for the first clinical finding.

19. The method of claim 10, further comprising inputting additional swipe gestures to the first tile to advance from the one of the additional images to either a different one of the additional images or the first image.

20. The method of claim 1, further comprising:
displaying a pop-up button with a plurality of statuses for the first clinical finding in response to said selecting the first anatomical zone, wherein the plurality of statuses are related to the presence of free fluid in the first anatomical zone, wherein the plurality of statuses include a first text string to indicate the presence of free fluid in the first anatomical zone, a second text string to indicate the absence of free fluid in the first anatomical zone, and a third text string to indicate that the presence of free fluid in the first anatomical zone is indeterminate;
interacting with the pop-up button via an interaction with a touchscreen to select one of the plurality of statuses; and
wherein said saving and associating the clinical finding with the first anatomical zone comprises saving and associated the selected one of the plurality of statuses with the first anatomical zone.

* * * * *